United States Patent [19]

Berry, Jr.

[11] Patent Number: 5,505,916

[45] Date of Patent: Apr. 9, 1996

[54] AUTOCLAVE CASSETTE

[75] Inventor: Bernie B. Berry, Jr., Indianapolis, Ind.

[73] Assignee: C/T Med—Systems Ltd. Inc., Indianapolis, Ind.

[21] Appl. No.: 414,037

[22] Filed: Mar. 30, 1995

Related U.S. Application Data

[63] Continuation of Ser. No. 127,441, Sep. 27, 1993, abandoned, which is a continuation of Ser. No. 935,157, Aug. 25, 1992, abandoned.

[51] Int. Cl.$^6$ ...................................................... A61L 2/06
[52] U.S. Cl. ........................... 422/300; 422/297; 206/439; 206/480; 206/483; 206/565
[58] Field of Search ........................ 422/104, 297, 422/300, 310; 206/210, 263, 363, 369, 370, 438, 439, 480, 483, 565

[56] References Cited

U.S. PATENT DOCUMENTS

| | | | |
|---|---|---|---|
| D. 295,074 | 4/1988 | Jerge et al. | D24/9 |
| D. 295,075 | 4/1988 | Jerge et al. | D24/9 |
| D. 318,329 | 7/1991 | Porteous | D24/217 |
| 857,240 | 6/1907 | Henning . | |
| 1,973,947 | 9/1934 | Enderle | 27/35 |
| 2,147,510 | 2/1939 | Amick | 206/263 X |
| 3,029,507 | 4/1962 | Gaggini | 72/348 X |
| 3,091,488 | 5/1963 | Vander Sande et al. | 292/241 |
| 3,179,287 | 4/1965 | Rickmeier, Jr. | 220/94 |
| 3,263,637 | 8/1966 | Cox | 72/348 X |
| 3,285,409 | 11/1966 | Loran | 206/63.5 |
| 3,433,269 | 3/1969 | Sackett, Sr. | 138/92 |
| 3,532,221 | 10/1970 | Kaluhiokalani et al. | 211/60 |
| 3,589,511 | 6/1971 | Britt | 206/65 |
| 3,634,937 | 1/1972 | Green | 32/1 |
| 3,636,748 | 1/1972 | Hall et al. | 72/349 |
| 3,890,096 | 6/1975 | Nichol et al. | 21/105 |
| 3,982,630 | 9/1976 | Garnier | 206/369 |
| 4,193,285 | 3/1980 | Zumsteg | 72/348 |
| 4,361,020 | 11/1982 | Hirota et al. | 72/348 X |
| 4,541,992 | 9/1985 | Jerge et al. | 422/300 |
| 4,572,371 | 2/1986 | Asenbauer | 206/443 |
| 4,643,303 | 2/1987 | Arp et al. | 206/370 |
| 4,774,063 | 9/1988 | Runnells | 422/297 |
| 4,826,348 | 5/1989 | Brightman | 403/330 |
| 4,852,738 | 8/1989 | Craig et al. | 206/369 |
| 4,854,475 | 8/1989 | Riihimaki et al. | 220/337 |
| 4,930,660 | 6/1990 | Porteous | 206/63.5 X |
| 4,959,199 | 9/1990 | Brewer | 422/300 |
| 5,002,319 | 3/1991 | Chandler | 292/17 |
| 5,004,418 | 4/1991 | Porteous | 433/77 |
| 5,031,768 | 7/1991 | Fischer | 206/438 X |
| 5,084,251 | 1/1992 | Thomas | 422/300 |
| 5,098,676 | 3/1992 | Brooks, Jr. | 422/292 |
| 5,173,273 | 12/1992 | Brewer | 422/310 X |
| 5,215,726 | 6/1993 | Kudla et al. | 422/297 |
| 5,294,413 | 3/1994 | Riihimaki et al. | 422/297 |
| 5,346,677 | 9/1994 | Risk | 422/297 |

FOREIGN PATENT DOCUMENTS 805909  6/1951  Germany .

*Primary Examiner*—Robert J. Warden
*Assistant Examiner*—Theresa T. Snider
*Attorney, Agent, or Firm*—Woodard, Emhardt, Naughton, Moriarty & McNett

[57] ABSTRACT

A metal autoclave cassette for dental instruments and appliances includes a pair of identical tray halves which are free of any outwardly extending flanges and which are provided with rounded corners and corner edges. Each tray half includes a retaining frame which is riveted in place and which includes a plurality of aligned recesses in the opposite ends. The recesses are used for the receipt of the elongate dental instrument's and a hold down mechanism clamps the instruments into position yet is easily moved out of position to provide access to the dental instruments.

11 Claims, 4 Drawing Sheets

5,505,916

AUTOCLAVE CASSETTE

This application is a continuation of application Ser. No. 08/127,441, filed Sep. 27, 1993, now abandoned, which is a continuation of application Ser. No. 07/935,157, filed Aug. 25, 1992, now abandoned.

BACKGROUND OF THE INVENTION

The present invention relates in general to autoclave trays, enclosures, and cassettes and in particular to metal cassettes for dental instruments and appliances. One aspect of importance in the design of autoclave trays and cassettes is the compactness relative to holding capacity and the related aspect of size compatibility with existing autoclaves. The present invention addresses this aspect in a manner which is novel and not heretofore provided.

Conventional design wisdom for autoclave trays and containers (often referred to as cassettes) is to create a tray, a closing lid and an interconnecting latch mechanism to hold the lid onto the tray. Typically the tray portion includes holders, clamps, fixtures and the like to receive and hold the medical, surgical or dental instruments and appliances. Secure retention of the instruments and appliances is important since during the autoclaving operation the cassette will be turned upside down as if in a tumbling action. If instruments or appliances come loose within the cassette their delicate points and edges could be nicked and marred, likely making the instrument or appliance unacceptable unless reworked and repaired or simply replaced.

The conventional design wisdom for autoclaves and cassettes also includes placing a large number of steam holes in the tray and lid. Further, the latch mechanism is frequently placed in conjunction with side flanges or handle portions. One drawback in having side flanges or side handle portions is that they detract from the compactness of the design. While they do provide a simple and convenient way by which to incorporate interlocking latches, these flanges take up space and do not contribute to the packaging density within the tray or cassette. These conventional designs also entail a number of separate component pieces all of which must be separately manufactured, assembled, stored, inventoried, etc. Autoclave cassette designs with a fewer number of different pieces would be desirable. The elimination of sharp corners or edges would also be a desirable improvement since this would add to user safety, comfort and reduce the risk that the paper used to wrap the sterile cassette would be punctured.

Autoclave tray and cassette design which might be of interest in order to appreciate some of the aspects of this conventional design system are disclosed in the following patents:

| Patent No. | Patentee | Issue Date |
| --- | --- | --- |
| 5,098,676 | Brooks, Jr. | March 24, 1992 |
| 5,002,319 | Chandler | March 26, 1991 |
| 1,973,947 | Enderle | Sept. 18, 1934 |
| 3,433,269 | Sackett, Sr. | March 18, 1969 |
| 4,826,348 | Brightman | May 2, 1989 |
| 3,179,287 | Rickmeier, Jr. | April 20, 1965 |
| 3,091,488 | Vander Sande et al. | May 28, 1963 |
| 805 909 | Külbel-Germany | June 4, 1951 |

Brooks discloses a plastic sterilization and storage container which includes a lower tray portion and an upper lid portion. Disposed within the tray portion is a finger mat for supporting surgical instruments. The tray and lid are molded out of plastic and each includes an outwardly extending flange portion with the lid flange fitting over and around the tray flange. A metal clamp then pivots from the plastic lid over and around the overlapping flanges as a means to clamp the lid onto the tray.

Chandler discloses a sheet metal latch apparatus which may be used to attach a cover or lid portion to a base container.

Enderle discloses a lid and container combination in which a pivoting U-shaped latch is used to clamp together the outwardly extending flanges of both members.

Sackett discloses a rapid access closure system in which a base container is covered by a lid each of which have an outwardly extending flange portion. The two flanges are secured together by a pin arrangement.

Brightman discloses a coupling set for interlocking objects which includes first and second coupling elements each having an integral stud by which it is anchored to one of two objects to be interlocked.

Rickmeier discloses a container and lid in combination each of which includes an outwardly extending flange portion. The lid is provided with a series of slot openings and the base container has a matching series of protruding extensions. A pivotal or swivel latch mechanism is attached to the lid and provides an interlocking arrangement when the lid is secured to the base container.

Vander Sande discloses a rotary latch mechanism for use in securing together a base container and lid member. In this particular arrangement there are no outwardly extending flanges and the rotary latch relies principally on a spring clip and pin arrangement for securing the hinged lid in a closed position on the base container.

The German patent discloses a hinged lid and tray combination including a front wall, two-part latch mechanism. The lid includes an extended pin and the base or tray portion includes a spring clip slot with inwardly protruding projections. The latching mechanism relies on the lid pin pushing through the tray projections and coming to rest at a point of clearance beneath the projections. The projections are spring biased such that when suitable force is exerted on the lid the pin can be pulled back through the protruding portions in order to open the container.

The autoclave cassette of the present invention departs from the conventional wisdom by providing a trim and streamlined cassette which maximizes the instrument density and eliminates some of the negatives with earlier designs such as the flanges and sharp corners. The present invention uses a drawn base and lid which are pinch trimmed for full face edge closing. The base and lid are identical thus reducing the number of different component parts which must be fabricated, assembled and inventoried in order to create this invention. The instrument retainers for each half are identical and there is effectively no wasted space within the cassette of the present invention. By the elimination of the flange it is possible to load nine or ten cassettes according to the present invention into a typical ten inch diameter autoclave.

SUMMARY OF THE INVENTION

An autoclave cassette according to the present invention includes a first tray including a plurality of steam holes, a second tray including a plurality of steam holes and having a construction which is the same in all respects as said first tray, a hinge attached to and between the first and second trays, a latch mechanism for retaining the first and second trays in a closed condition and retaining brackets disposed within and attached to each of the first and second trays for securing a plurality of items to be autoclaved.

One object of the present invention is to provide an improved autoclave cassette.

Related objects and advantages of the present invention will be apparent from the following description.

DESCRIPTION OF THE PREFERRED EMBODIMENT

Figure 1:
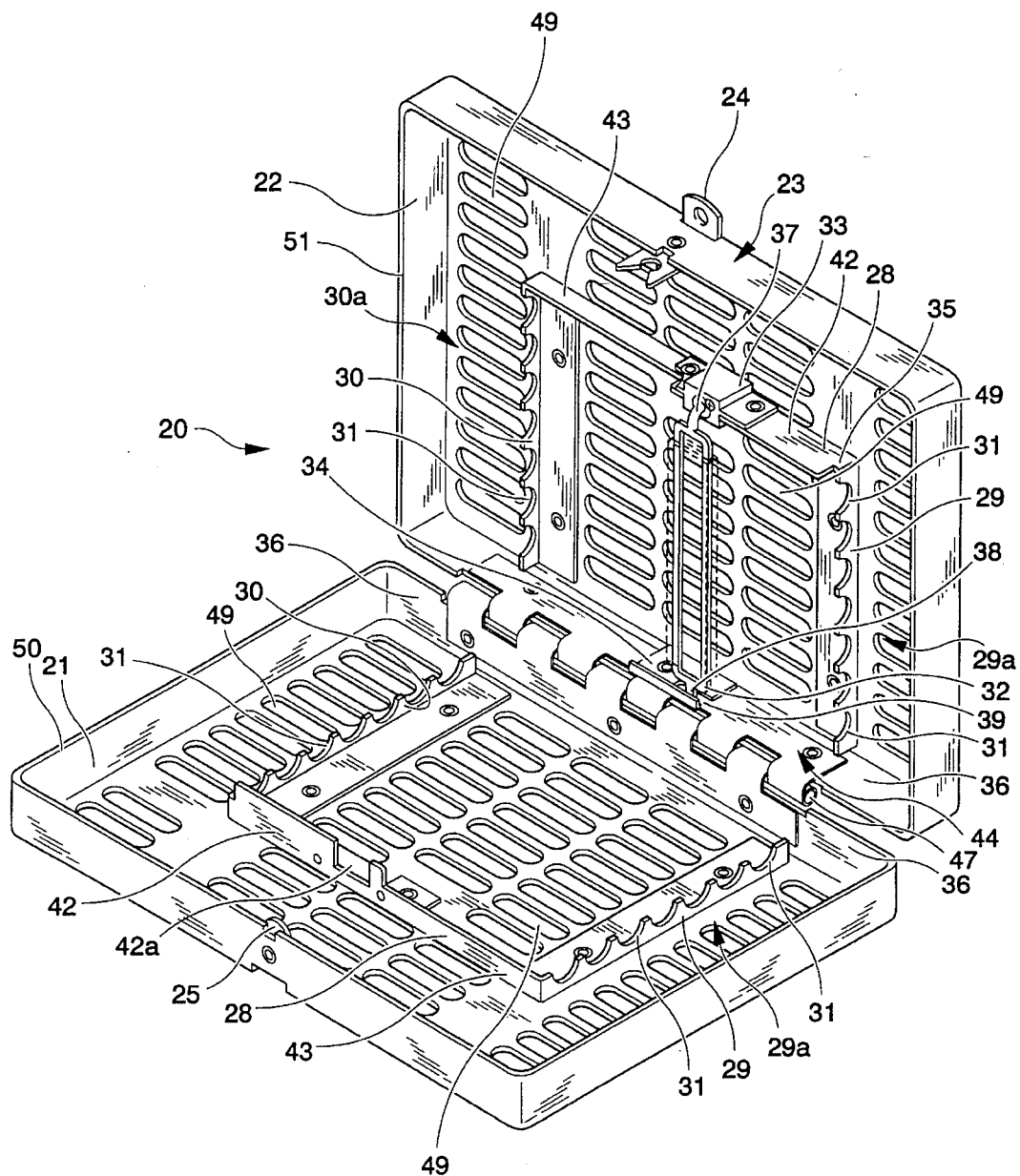
FIG. 1 is a perspective view of an autoclave cassette according to a typical embodiment of the present invention.

For the purposes of promoting an understanding of the principles of the invention, reference will now be made to the embodiment illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

Referring to FIG. 1 there is illustrated an autoclave cassette 20 for dental instruments and appliances. The cassette 20 includes a pair of drawn, generally rectangular trays 21 and 22 which are in effect tray halves and are identical in size, shape and hole patterns. The only difference between the two tray halves relates to the two-piece latch 23 where the slide portion 24 is riveted to the front wall of tray 22 and the retainer portion 25 is riveted to the front wall of tray 21. However, trays 21 and 22 are still machined in an identical fashion such that the slide portion 24 and the retainer portion 25 can be attached to the front wall of either tray, interchangeably. The slide portion 24 has a split bayonet design with a narrow slit extending into an enlarged opening. The retainer portion 25 has a shouldered pin having an enlarged head which is received within and anchored by the slide portion 24.

Figure 2:
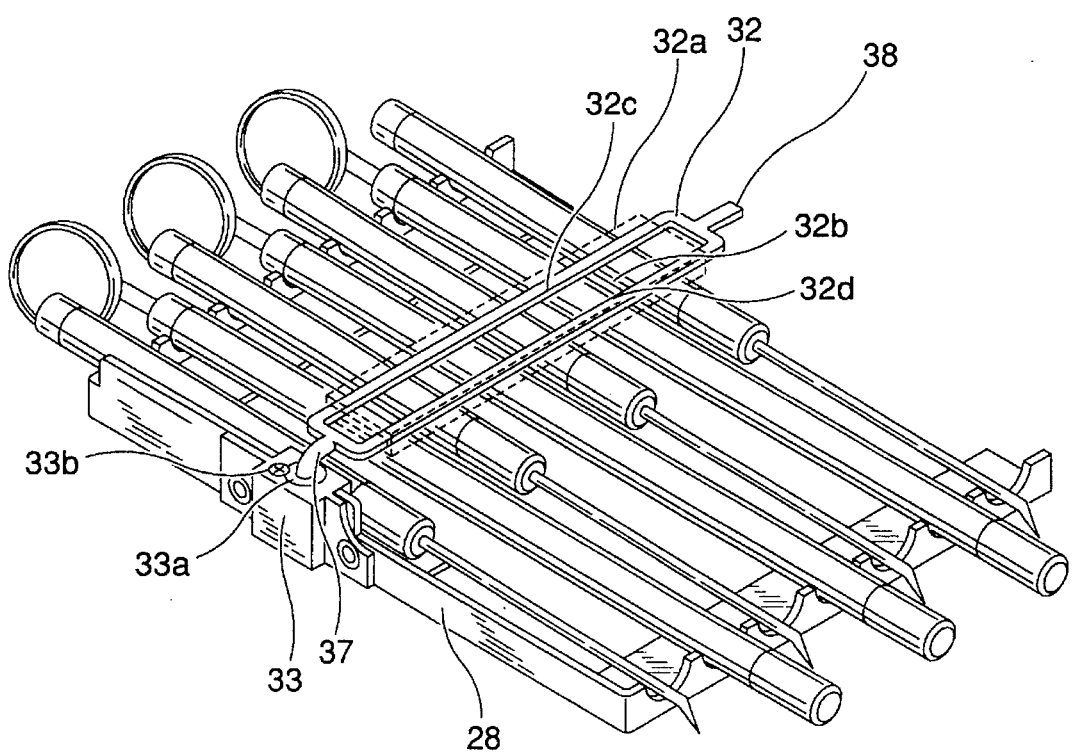
FIG. 2 is a perspective view of a retaining bracket which is assembled in the FIG. 1 cassette, illustrating dental instruments retained therein.
Figure 3:
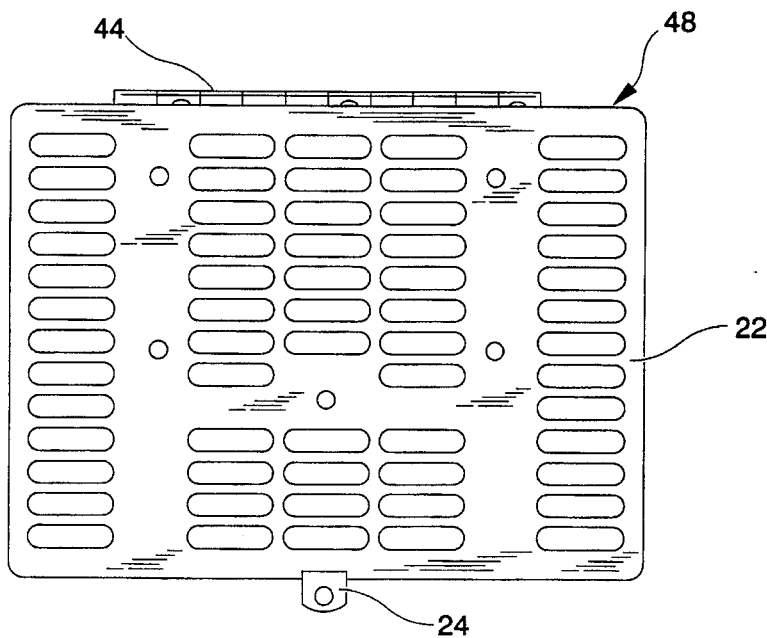
FIG. 3 is a top plan view of the FIG. 1 cassette in a closed condition.
Figure 4:
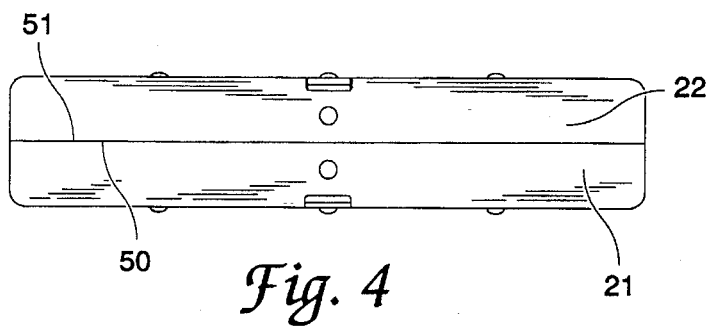
FIG. 4 is a front elevational view of the FIG. 1 cassette in a closed condition.
Figure 5:
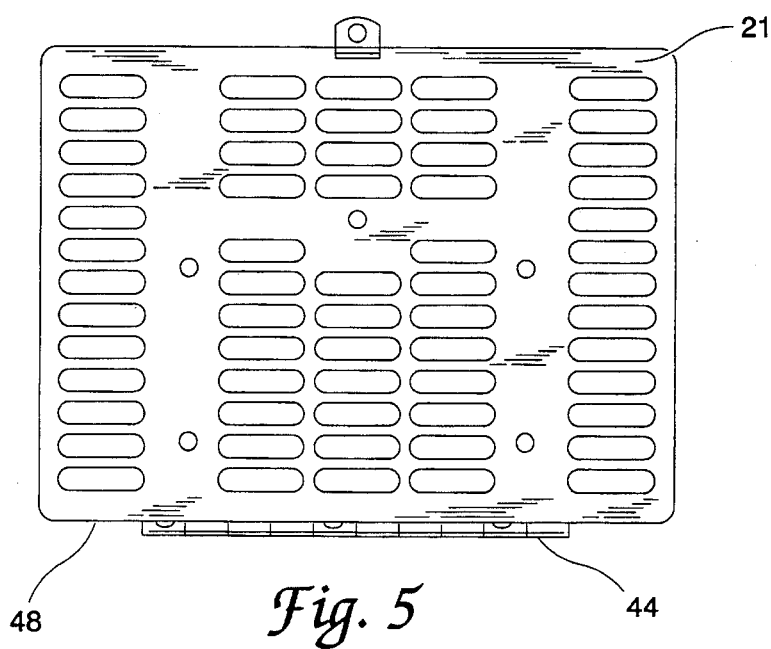
FIG. 5 is a bottom plan view of the FIG. 1 cassette in a closed condition.
Figure 6:
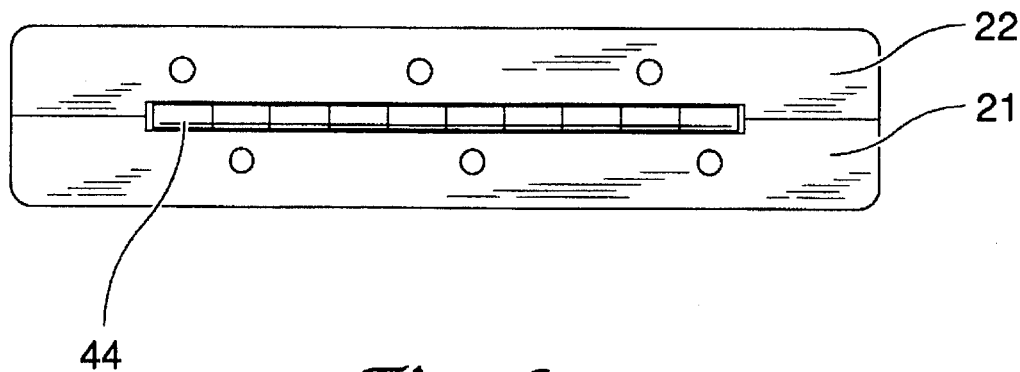
FIG. 6 is a rear elevational view of the FIG. 1 cassette in a closed condition.
Figure 7:
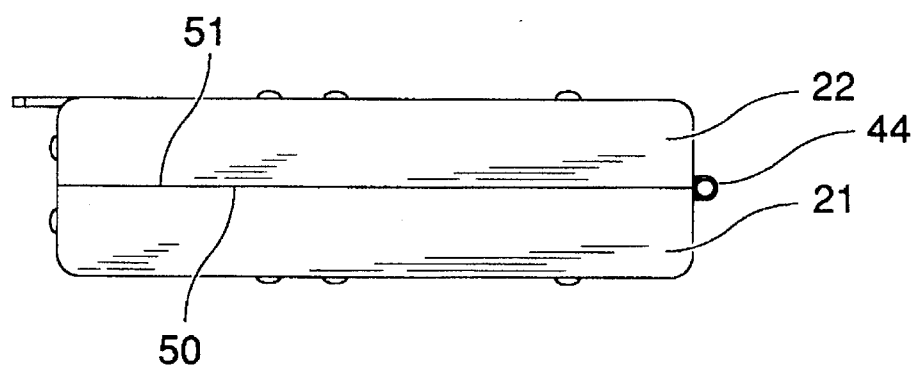
FIG. 7 is a side elevational view, from the right side, of the FIG. 1 cassette in a closed condition.

Riveted in place to the base or bottom surface of each tray is a three-sided, part-rectangular instrument retainer frame 28 configured with opposite end walls 29 and 30 each of which are contoured with seven curved recesses 31. The curved recesses 31 in each end wall are aligned with the opposite wall so as to in effect provide a straight channel which is used to support and retain dental instruments and appliances, see FIG. 2.

Retainer 32 which is disposed only in tray 22 serves to hold the dental instruments in both tray halves (i.e., in retainer frames 28) when the cassette is closed. Retainer 32 is received at one end by pivot block 33 and at the opposite end by slotted bracket 34. Retainer 32 will typically be partially covered by a resilient, flexible sleeve (noted by the broken line 32a) which serves as a resilient cushion against the dental instruments which are loaded into the two frames 28. The sleeve is preferably constructed from an extruded silicone material. The resilient member, though typically a sleeve, may alternatively be a flexible, resilient member such as a tube or rod which is wedged into opening 32b to provide the cushioned compression on the dental instruments. In this manner the retainer 32 is designed to securely hold down the dental instruments and appliances which are loaded into frame 28 of tray 22. By placing tray 21 on a horizontal surface, the instruments in frame 28 of tray 21 will be held in position by gravity. Retainer 32 must still clamp the instruments in tray 22 while the tray 22 opens as the cassette lid. When the lid (tray 22) is closed for autoclaving the retainer acts on both sets of dental instruments concurrently.

Retainer 32 includes a generally planar main body portion which is constructed with two substantially parallel arms 32c and 32d which provide two spaced-apart pressure points on each instrument so as to prevent rocking or tilting of the instruments as might occur with only a single pressure point. Examples of the types of dental instruments or appliances which may be retained in frame 28 include dental mirrors and picks. Each of these devices is elongate and typically has a length dimension such that it will extend beyond the end walls 29 and 30 of frame 28. For this reason each frame is inset from the side walls of the corresponding tray leaving clearance spaces 29a and 30a at each end. Since the dental devices can be oriented in either direction in the recesses 31 of frame 28, it may be either the handle portion or the tip portion of each device which extends beyond the frame into the clearance spaces. It is also possible to orient these instruments in an alternating or reverse direction depending on the preferences of the dentist or dental assistant.

The area left between the front wall of each frame and the front wall of the corresponding tray half may be used for other dental instruments and appliances which are either too large to fit within the aligned recesses 31 of frame 28 or which may be too small to be received in that they will not extend that distance. For small items a wire screen or mesh container may be used for storage during autoclaving. Such container or containers are sized to fit in the clearance area between the front wall of the frame and the front wall of the tray half. However, for larger items and for any small article containers, the clearance depth of both trays would likely be required as contrasted with items retained in the retainer frame 28. Consequently, two frames can be used due to the article height enabling a total of 14 instruments or appliances to be retained in the frames of each individual cassette in addition to whatever larger articles or smaller items may be placed in the front clearance area.

Pivot block 33 is riveted in place to the front wall 35 of retainer frame 28 in tray 22. The slotted bracket 34 is riveted in place to the rear wall 36 of tray 22. As illustrated the rivet which attaches the slotted bracket 34 to the rear wall 36 actually extends through one flange of the hinge such that the center rivet actually secures the slotted bracket and one flange of the hinge and the rear wall 36 of tray 22 all together.

In use, one end 37 of retainer 32 is pivotably retained in block 33 and the opposite end 38 of the retainer 32 fits within in slot 39. Block 33 includes a cylindrical bore into which a bearing sleeve 33a is placed and end 37 is axially retained in the sleeve. Screw 33b extends over the edge of the sleeve 33a so that the sleeve cannot be withdrawn from the cylindrical bore without first removing the screw 33b. When a dental instrument or appliance is to be removed from the frame, the opposite end 38 is pulled out of slot 39. This motion is permitted by the pivotal connection of end 37 within block 33. With retainer 32 pivoted out of the way, after tray 22 is placed in a fully opened condition on a horizontal surface, all of the instruments or appliances loaded in frame 28 of the tray 22 then become accessible and can be easily lifted out of the aligned recesses. The instruments in frame 28 of tray 21 become accessible once tray 22 is opened as this lifts retainer 32 off of these instruments.

The front wall 35 of each retainer frame 28 is offset with a raised portion 42 and a lower portion 43. The pivot block 33 fits within a relief notch 42a (not visible in FIG. 2, see the lower retainer frame in FIG. 1) and is riveted to the raised portion of frame 28 in tray 22. Pivot block 33 is mounted near the geometric center of the retainer frame 28 between the opposite end walls 29 and 30. It is to be noted that the two retainer frames are positioned in an identical fashion in their corresponding trays 21 and 22 causing the frame edges to be aligned when the trays are closed together. The two frames are fashioned in an identical manner even though only one receives retainer 32. This identical construction permits the use of a single frame style regardless of the tray to which it is assembled. This positioning enables the two trays 21 and 22 to close together securely without interference and for a single retainer 32 to be used for clamping both sets of dental instruments.

The two trays are hinged together by continuous hinge 44 and the hinge flanges 45 and 46 are bent back relatively to the longitudinal axis of pivot pin 47 to enable the inner edge of the hinge knuckle to be positioned nearly flush with the outer rear surface 48 of each tray. The hinge knuckle is mounted with minimum clearance, just enough to permit the tray halves to be fully opened and lay flat on the same horizontal surface. Flange 45 is riveted to the rear wall 36 of tray 21 and flange 46 is riveted to the rear wall of tray 22. While the three rivet holes in tray 21 are not symmetrical between the tray ends or side walls, when one tray is turned relative to the other so as to create the clam-shell enclosure, the two sets of rivet holes will be staggered from each other. However, this particular stagger works well with the hinge design as is illustrated and thus the rivet holes in the hinge are provided in an offset manner to match the rivet holes in the two tray halves. It is still to be understood that the two trays are identical and the stagger is created when one is turned relative to the other. The hinge hole stagger also means that the rivet heads will not abut against each other when the cassette is fully opened and flat. This means that both tray halves 21 and 22 can lay flat and will not rock as might be the case if the rivet heads were in contact.

Trays 21 and 22 are fabricated without any flanges or sharp corners. The smooth, trim and compact nature of cassette 20 is illustrated in FIGS. 3 through 7. These drawing figures also illustrate the number, shape and spacing of steam holes 49. Trays 21 and 22 are fabricated out of an aluminum alloy by a drawing process after which the edges are pinch trimmed. NC milling is used to establish the finished height of each tray. A two-station perforating die is used for the oblong steam holes. Horn dies are used to punch the latch holes and rivet holes. The abutting edges 50 and 51 of trays 21 and 22, respectively, are smooth and flat enabling a tight fit of the two trays when they are hinged and closed together. The drawing process enables the rounded corners for each tray and the use of a hinge precludes the need for a separate or detachable lid. The slide latch precludes the need for any flanges that would typically be used for securing latches or spring clamps. The result of this combination is a very smooth, efficient and compact design which provides maximum appliance or instrument density.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

What is claimed is:

1. An autoclave cassette comprising:

a first drawn metal tray having a front wall, an oppositely disposed rear wall and a base panel and including means defining a plurality of sterilant apertures;

a second drawn metal tray having a front wall, an oppositely disposed rear wall and a base panel and including means defining a plurality of sterilant apertures and having a construction which is identical to said first drawn metal tray;

a continuous hinge having a first hinge flange attached to the rear wall of said first drawn metal tray and a second hinge flange attached to the rear wall of said second drawn metal tray so as to retain said first and second drawn metal trays together as a single unit and so as to enable the second drawn metal tray to hingedly open off of said first drawn metal tray;

latch means having a first portion attached to the front wall of said first drawn metal tray and a second portion attached to the front wall of said second drawn metal tray for retaining said first and second drawn metal trays in a closed condition;

a first instrument retainer attached to the base panel of said first drawn metal tray;

a second instrument retainer attached to the base panel of said second drawn metal tray; and a hold down bar attached to said second instrument retainer so as to clamp instruments retained therein, said hold down bar cooperatively arranged with said first instrument retainer with said first and second drawn metal trays in a closed condition so as to secure instruments retained in said first instrument retainer.

2. The autoclave cassette of claim 1 wherein the first and second drawn metal trays are free of any outwardly extending flanges.

3. The autoclave cassette of claim 1 wherein said first and second instrument retainers are each configured as a three-sided generally rectangular frame with opposite end walls having a plurality of aligned recesses for receiving dental instruments.

4. An autoclave cassette for medial and dental instruments comprising:

a first tray member;

a second tray member;

a hinge attached to and between said first and second tray members;

two-part latch means for retaining said first and second tray members in a closed condition, one part of said means being assembled to said first tray member and the other part of said latch means being assembled to said second tray member; and retention means assembled to one of said tray members for receiving and securing instruments, said retention means including a receiving frame with a plurality of receiving channels;

a pivot block attached to said receiving frame and having means defining an axial, generally cylindrical aperture; and a hold down bar, said hold down bar having a generally planar main body, a pivot post at a first end of said main body and a locking stem at a second, opposite end of said main body, said pivot post being received by said axial, generally cylindrical aperture.

5. The autoclave cassette of claim 4 which further includes a flexible sleeve secured to said generally planar main body for cushioning the securing of instruments by said hold down bar.

6. A retention assembly for receiving and securing dental instruments comprising:

a receiving frame with a plurality of receiving channels;

a pivot block attached to said receiving frame and having means defining an axial, generally cylindrical aperture; and a hold down bar, said hold down bar having a generally planar main body, a pivot post at a first end of said main body and a locking stem at a second, opposite end of said main body, said pivot post being received by said axis, generally cylindrical aperture.

7. The retention assembly of claim 6 which further includes a flexible sleeve secured to said generally planar main body for cushioning the securing of instruments by said hold down bar.

8. An autoclave cassette comprising:

a first drawn metal tray having a front wall, an oppositely disposed rear wall and a base panel and including means defining a plurality of sterilant apertures;

a second drawn metal tray having a front wall, an oppositely disposed rear wall and a base panel and including means defining a plurality of sterilant apertures and having a construction which is identical to said first drawn metal tray;

means for securing said first and second drawn metal trays together in a hinged arrangement whereby said first and second drawn metal trays are moveable between an opened orientation and a closed orientation;

a first instrument retainer attached to the base panel of said first dawn metal tray;

a second instrument retainer attached to the base panel of said second drawn metal tray; and a hold down bar attached ho said second instrument retainer so as to secure instruments retained therein, said hold down bar cooperatively arranged with said first instrument retainer with said first and second drawn metal trays in said closed orientation so as to clamp instruments retained in said first instrument retainer.

9. An autoclave cassette comprising:

a first drawn metal tray having a front wall, an oppositely disposed rear wall and a base panel and including means defining a plurality of sterilant apertures;

a second drawn metal tray having a front wall, an oppositely disposed rear wall and a base panel and including means defining a plurality of sterilant apertures and having a construction which is identical to said first drawn metal tray;

a latch bracket attached to the rear wall of said second drawn metal tray;

a continuous hinge having a first hinge flange attached to the rear wall of said first drawn metal tray and a second hinge flange attached to the rear wall of said second drawn metal tray so as to retain said first and second drawn metal trays together as a single unit and so as to enable the second drawn metal tray to hingedly open off of said first drawn metal tray;

latch means having a first portion attached to the front wall of said first drawn metal tray and a second portion attached to the front wall of said second drawn metal tray for retaining said first and second drawn metal trays in a closed condition;

a first instrument retainer attached to the base panel of said first drawn metal tray;

a second instrument retainer attached to the base panel of said second drawn metal tray and including a support member; and a hold down bar for clamping against and thereby securing instruments retained in said second instrument retainer, said hold down bar having a captured end received in said support member and an oppositely disposed latching end removably secured within said latch bracket and a clamping portion disposed between said captured end and said latching end, said captured end being cooperatively arranged with said support member to enable movement of said latching end out of said latch bracket and to thereafter enable said clamping portion to move relative to said second instrument retainer so as to move out of clamping engagement with instruments positioned in said second instrument retainer, said hold down bar cooperatively arranged with said first instrument retainer with said first and second drawn metal trays in a closed condition so as to clamp instruments retained in said first instrument retainer.

10. An autoclave cassette comprising:

a first drawn metal tray having a front wall, an oppositely disposed rear wall and a base panel and including means defining a plurality of sterilant apertures;

a second drawn metal tray having a front wall, an oppositely disposed rear wall and a base panel and including means defining a plurality of sterilant apertures and having a construction which is identical to said first drawn metal tray;

a latch bracket attached to the rear wall of said second drawn metal tray;

a first instrument retainer attached to the base panel of said first drawn metal tray;

a second instrument retainer attached to the base panel of said second drawn metal tray; and a hold down bar for clamping against and thereby securing instruments retained in said second instrument retainer, said hold down bar having a captured end received in said second instrument retainer and an oppositely disposed latching end removably secured within said latch bracket and a clamping portion disposed between said captured end and said latching end, said captured end being cooperatively arranged with said second instrument retainer to enable movement of said latching end out of said latch bracket and to thereafter enable said clamping portion to move relative to said second instrument retainer so as to move out of clamping engagement with instruments positioned in said second instrument retainer, said hold down bar cooperatively arranged with said first instrument retainer with said first and second drawn metal trays in a closed condition so as to clamp instruments retained in said first instrument retainer.

11. An autoclave cassette comprising:

a first drawn metal tray having a front wall, an oppositely disposed rear wall and a base panel and including means defining a plurality of sterilant apertures, said first drawn metal tray being free of any outwardly extending flanges;

a second drawn metal tray having a front wall, an oppositely disposed rear wall and a base panel and including means defining a plurality of sterilant apertures, said second drawn metal tray being free of any outwardly extending flanges, and having a construction which is identical to said first drawn metal tray;

a continuous hinge having a first hinge flange attached to the rear wall of said first drawn metal tray and a second hinge flange attached to the rear wall of said second drawn metal tray so as to retain said first and second drawn metal trays together as a single unit and so as to enable the second drawn metal tray to hingedly open off of said first drawn metal tray;

latch means having a first portion attached to the front wall of said first drawn metal tray and a second portion attached to the front wall of said second drawn metal tray for retaining said first and second drawn metal trays in a closed condition;

a first instrument retainer attached to the base panel of said first drawn metal tray, and being configured as a three sided generally rectangular frame with opposite end walls having a plurality of aligned recesses for receiving dental instruments;

a second instrument retainer attached to the base panel of said second drawn metal tray, and being configured as a three sided generally rectangular frame with opposite end walls having a plurality of aligned recesses for receiving dental instruments; and a hold down bar attached to said second instrument retainer so as to secure instruments retained therein, said hold down bar cooperatively arranged with said first instrument retainer with said first and second drawn metal trays in a closed condition so as to clamp instruments retained in said first instrument retainer.

* * * * *